United States Patent [19]
Blanchett et al.

[11] Patent Number: 6,152,883
[45] Date of Patent: Nov. 28, 2000

[54] KLT-BASED QUALITY CONTROLLED COMPRESSION OF A SINGLE LEAD EGG

[75] Inventors: Travis Paul Blanchett, Dartmouth; Guy Cecil Kember, Waverley; Gordon Ashley Fenton, Halifax, all of Canada

[73] Assignee: Dalhousie University, Canada

[21] Appl. No.: 09/338,828

[22] Filed: Jun. 23, 1999

Related U.S. Application Data

[60] Provisional application No. 60/090,330, Jun. 23, 1998.

[51] Int. Cl.[7] .................................................. A61B 5/04
[52] U.S. Cl. ........................ 600/521; 600/509; 600/516
[58] Field of Search ................................... 600/508, 509, 600/515, 516, 517, 521

[56] References Cited

U.S. PATENT DOCUMENTS

| | | |
|---|---|---|
| 4,947,858 | 8/1990 | Smith . |
| 5,090,418 | 2/1992 | Squires et al. .......................... 600/515 |
| 5,215,098 | 6/1993 | Steinhaus et al. . |
| 5,263,486 | 11/1993 | Jeffreys . |
| 5,560,368 | 10/1996 | Berger . |
| 5,623,935 | 4/1997 | Faisandier . |
| 5,657,398 | 8/1997 | Guilak . |
| 5,967,995 | 10/1999 | Shusterman et al. ................... 600/516 |

FOREIGN PATENT DOCUMENTS

| | | |
|---|---|---|
| 2149670 | of 0000 | Canada . |
| 2161976 | of 0000 | Canada . |
| 1244092 | 11/1988 | Canada . |

OTHER PUBLICATIONS

Lux et al., "Redundancy Reduction For Improved Display And Analysis of Body Surface Potential Maps, I. Spatial Compression", Circulation Research, vol. 49, pp. 186–196.

Hsu et al., "Simultaneous Noise Filtering adn Data Compression of ECG's", Biomedical Science Instr., vol. 17, 1981.

Jalaleddine, Sateh M.S., Chriswell G. Huchens, Robert D. Strattan, and William A. Coberly. "ECG Data Compression Techniques—A Unified Approach," IEEE Transactions on Biomedical Engineering 37(4), Apr. 1990, 329–343.

Cetin, A. Enis, Hayrettin Koymen, and M. Cegiz Aydin. "Multichannel ECG Data Compression by Multirate Signal Processing and Transform Domain Coding Techniques," IEEE Transactions on Biomedical Engineering 40(5), May 1993, 495–499.

*Primary Examiner*—Cary O'Connor
*Assistant Examiner*—Navin Natnithithadha
*Attorney, Agent, or Firm*—Jennifer L. Bales; Macheledt Bales & Johnson LLP

[57] ABSTRACT

A compression algorithm for the compression of ECG recordings uses the Karhunen-Loeve Transform (KLT) to transform a set of N sampled ECG beats from a matrix of N×M samples into a new form, from which a selected subset can be retained for storage, transmission, or analysis. In order to reduce computation time and storage space, a multirate downsampling operation may be applied, which retains the appropriate spectral information in each block. The downsampled beats are then padded to make them of uniform size, and a Karhunen-Loeve Transform is applied to the sample set. Coefficients from the Karhunen-Loeve Transform of the sample set are retained for reconstruction according to one of two criteria. The average variance of the reconstructed sample set may be controlled, or different numbers of coefficients may be retained for each beat. The KLT compressed data may be reconstituted by reverse KLT transforming the data.

29 Claims, 5 Drawing Sheets

KLT-BASED QUALITY CONTROLLED COMPRESSION OF A SINGLE LEAD EGG

This application claims the benefit of U.S. Provisional Application No. 60/090,330, filed Jun. 23, 1998.

BACKGROUND OF THE INVENTION

1. Field of the Invention

This invention relates to compression and automated analysis of electrocardiograms and other signals having recurring features with occasional significant deviations.

2. Description of the Prior Art

The correct medical diagnosis of heart problems often depends upon the analysis of ECG signals. Where a heart problem is intermittent or irregular, it becomes necessary to record these ECG signals, sometimes while the patient is performing normal every-day activities. Additionally, even for those patients with repeatable heart problems, there is a need to record and archive ECG signals for subsequent analysis and future comparison purposes, or to identify signal changes over time.

Traditionally ECG records have been created on either long-scroll paper or on analog-technology tape recordings. Whilst both these methods provide accurate imagery for subsequent analysis purposes, they are bulky to archive and are only suitable for short term recordings (a few minutes to 0.5 hours). In more recent times, use has been made of digital technology to a) convert the analog ECG signal to digital samples at a suitably selected rate and resolution, and b) store the digital samples on a suitable storage media such as computer memory, computer disks or digital tape recordings. Whilst this mechanism has increased storage time, storage media choices, and provides the possibility of computer enabled analysis of signals, there are still very real limitations in the length of recording time possible without severe limitations on sampling rates and signal resolution. If sampling rate and signal resolution are lowered to reduce the size and number of digital samples to be recorded, thus increasing possible recording time, unacceptable degradation to the reconstituted signal occurs from a clinical analysis point of view. Hence all commercially available ECG recording devices use some form of compression of the digital signal to increase the recording time possible on a given size of storage media.

A large number of compression algorithms have been developed and a variety of them are in use in current commercial devices. Compression algorithms are traditionally categorized into two classes, non-lossy and lossy. Non-lossy algorithms have the property that the original digital signal prior to compression can be completely reconstituted. These compression algorithms generally rely on removing duplicate or repeated information, in some form, from the original digital signal. Such techniques as run-line encoding and difference recording in various forms, are at the heart of most non-lossy compression algorithms. However, fundamentally such algorithms are limited in the amount of compression possible—there is only so much redundancy in a given signal that can be removed.

Lossy compression has the potential to achieve much greater compression factors than lossless compression algorithms, permitting greater archiving capacities or reductions in data storage. These lossy algorithms are therefore of great interest for ECG recording compression purposes.

ECG traces are characterized by a high rate of regularity from signal to signal, and dramatic differences in the range of signal frequencies present in different portions of a trace. For clinical purposes, certain portions of the ECG are of great significance.

A heartbeat is naturally divided into three segments, which are known as the PQ, QRS, and ST blocks. The R-peak of an ECG is an easily identified feature which occurs roughly in the center of the QRS-block. The PQ-block occupies ⅖ of the time from the current beat's R-peak back to the previous beat's R-peak, less the portion which is devoted to the QRS-block. Similarly, the ST-block occupies ⅗ of the time forward from the current beat's R-peak to the next beat's R-peak, less the portion which is devoted to the QRS-block. The ECG sampling frequency is typically chosen to resolve the QRS-complex, which has a larger range of frequencies than the PQ- and ST-blocks; the latter blocks are therefore significantly oversampled. Many of the features of clinical interest occur in the QRS-complex.

Lossy compression algorithms that are not designed to preserve these significant portions of the ECG will usually achieve high compression ratios only at the expense of these higher-frequency, clinically significant features in the ECG signal. For diagnostic applications in cardiology, the loss of this information is unacceptable. Therefore, lossy algorithms have been, for the most part, of extremely limited use in these diagnostic applications.

Another area in which significant gains in technology would be of great benefit is in the analysis portion of the clinical process. When there is reason to believe that a heart event of clinical significance has occurred during a long ECG recording, a technician must review the entire length of the ECG to locate the event; this is typically done manually, without any form of automatic recognition. That portion of the recording is then passed to a cardiologist for a more careful review, and for diagnosis. When the recording is extremely lengthy, this reviewing process is extremely time-consuming and tiresome for the technician; for these reasons, it is an error-prone process. Consequently, there is a need for an automated review process for ECG recordings; a highly sensitive automated review algorithm could be used to automatically identify potential significant events in a long ECG recording for further scrutiny by a technician, greatly reducing the time required to analyze the trace, and making the process less error-prone for the technician. Due to the highly localized nature of ECG signal changes during significant events, this automatic identification of significant events is extremely difficult to do when the signal is analyzed in the time or frequency domain alone. The theoretically optimal choice of transform domain for the representation of variations in signals is given by the Karhunen-Loeve Transform.

The Karhunen-Loeve Transform (KLT) is an analysis tool which has long been recognized as a useful means of localizing signal irregularities in a sample of signals which are of uniform length. It is particularly useful in analyzing signal samples where there is a great deal of similarity from signal to signal, when a great deal of the variance present in a signal sample can be captured in a few coefficients of the KLT. The KLT is an orthonormal basis transformation which, when computed for a specific set of signal samples, has the following properties relative to the signal sample:

It is the optimal decorrelating transform for the signal sample; that is, each coordinate of the transformed signal sample, viewed as a random variable on the signal sample, is uncorrelated with every other coordinate.

If the basis elements of the KLT for a given signal sample are arranged in decreasing order of the variance captured in the corresponding coordinates, then the mean square error of representation for an element of the signal sample is minimized over all possible representations of length m when the first m basis elements are used to represent a signal.

The KLT is calculated by first computing the covariance matrix for the signal sample. If the signals in the sample are of length K, then the covariance matrix is a K by K matrix whose (k,j) coordinate is the cross-covariance of the k coordinate and the j coordinate of a signal sample, viewed as a pair of random variables. This matrix is symmetric; a well-known theorem states that it is therefore diagonalizable. The basis transformation into a complete set of eigenvectors for the matrix constitutes the Karhunen-Loeve for the signal sample.

The KLT is clearly dependent on the characteristics of the signal sample; the basis vectors for the KLT are of a form completely dependent on the sample, and therefore no fast algorithms for calculating the exact transform in all cases is known. For the general sample of length K, the calculation of the KLT is an algorithm of complexity $K^3$. In cases where the sample length is high, and the characteristics of the sample are well understood, suboptimal decorrelating transforms (such as the Discrete Cosine Transform, in the case of many audio signals) are sometimes used in place of the KLT to keep computational complexity, and the cost of transformation, down.

Typical error measures applied to signal compression, for example, signal-to-noise ratio, mean-squared error, and root-mean squared error, are based on average reconstruction error, and hence are insensitive to individual waveform departures from the typical waveform. In medical signal analysis, which includes ECG analysis, such localized departures from typical signal behaviour are of clinical interest and are often evidence of pathology. Using an error control technique based on average error leads to potentially large localized reconstruction errors, and hence the potential loss of clinically significant information. A need remains in the art for a compression scheme capable of automatically detecting and correcting for localized departures from typical signal behaviour, in order to provide a high compression ratio and allow clinically acceptable reconstruction.

SUMMARY OF THE INVENTION

The present invention comprises an algorithm for the compression of ECG recordings. The compression algorithm can optionally reduce computation time and storage space required by exploiting the differing spectral densities in the PQ, QRS, and ST blocks of a heartbeat to apply a multirate downsampling operation that retains the appropriate spectral information in each block. The downsampled beats are then padded to make them of uniform size, and a Karhunen-Loeve Transform is applied to the sample set.

The most significant coefficients from the Karhunen-Loeve Transform of the sample set are retained for reconstruction according to one of two criteria. The first criterion, a variance criterion, retains the same number of coefficients for all beats in the sample; the number of coefficients is chosen so that the average variance of the reconstructed sample set is controlled.

The second criterion, a quality-controlled criterion, retains different numbers of coefficients for each beat. The number of coefficients for an individual beat is chosen so that the reconstruction error in individual blocks of the ECG is controlled.

The lossy compression algorithm for ECG signals, implemented via a transform, makes two significant advances. It overcomes the problem of loss of clinically significant resolution in the signal which is reconstituted from the compressed signal.

It provides a natural means for automating the identification of clinically significant events, which can be accomplished entirely within the transform domain, i.e., before the signal is reconstituted using the inverse algorithm.

This compression algorithm has the potential for implementation in a device which can automatically detect significant heart events as they occur, therefore eliminating the need for costly recording of large numbers of insignificant heart events during the monitoring period. This innovation would dramatically increase the possible recording time for a device, would speed up the diagnostic process, and would minimize the need for storage space.

Since the compression algorithm allows real-time identification of significant heart events, there is also the long-term potential for its employment in cardiologically corrective devices, such as pacemakers, where corrective medical procedures or medicines might need to be automatically applied.

DETAILED DESCRIPTION OF THE PREFERRED EMBODIMENTS

The present invention consists of an adaptive compression algorithm which employs a multi-rate sampling scheme based on prior knowledge of signal behaviour; the Karhunen-Loeve transform (KLT transform) to preserve significant variations in signals; and a locally measured relative error control technique.

Figure 1:
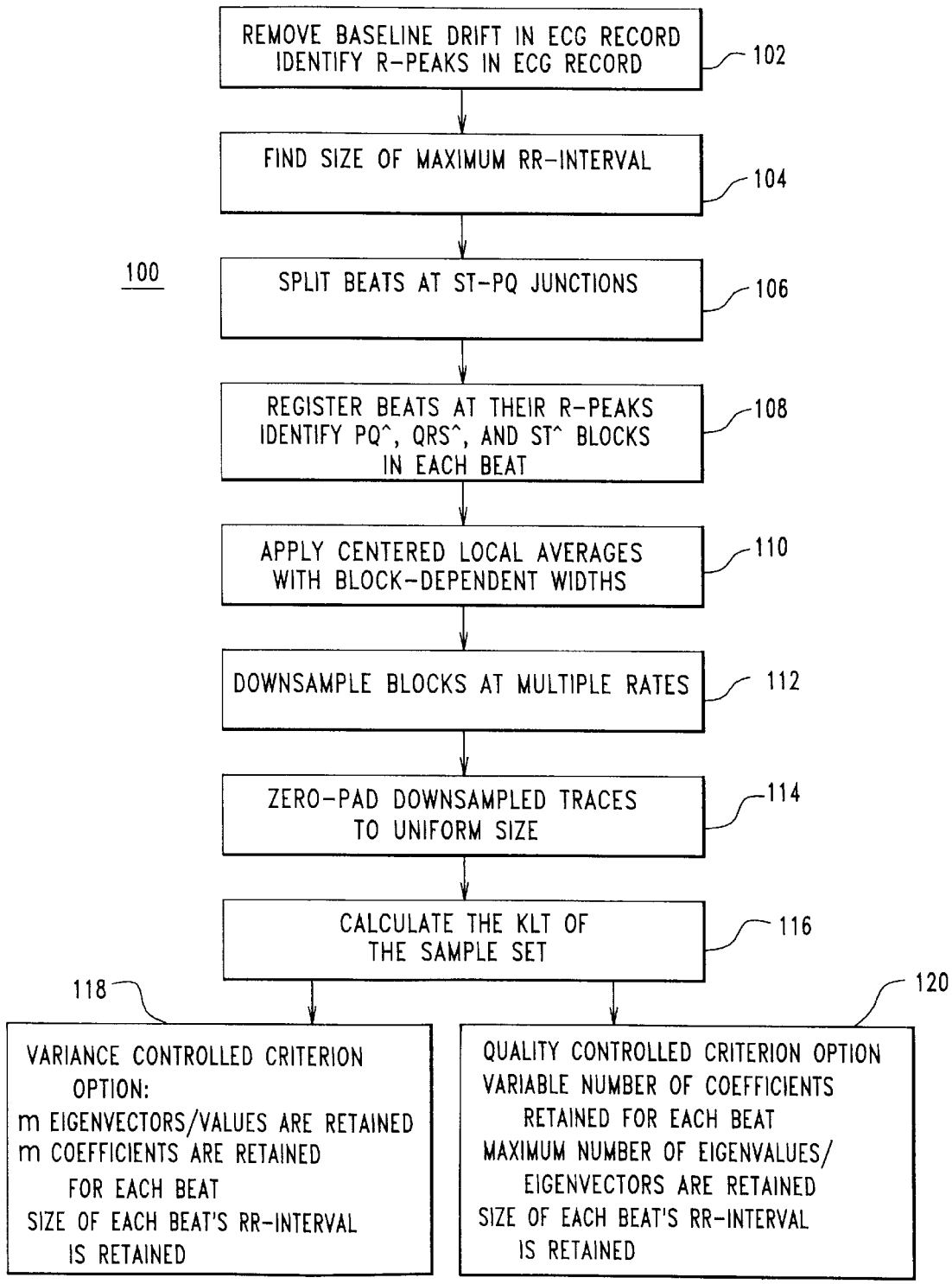
FIG. 1 is a flow diagram showing the flow of a compression algorithm according to the present invention.

FIG. 1 is a functional flow diagram of ECG compression algorithm 100, which is independently applied to every ECG data segment (for example a segment could be of 10 minutes duration). In step 102, the analysis of an ECG record begins by removing the baseline drift component from the ECG record. This is done by subtracting a one-second wide, centered moving average from the entire record. The R-peaks are then located in the record. R-peaks in an ECG trace are distinctive diagnostic features, which are easily identified. These peaks will serve as reference points to assist with the task of segmenting individual heartbeats.

An RR-interval in an ECG record is defined as the interval from one R-peak to the next. The number of samples in RR-intervals is variable. In step 104, the size of the largest RR-interval, denoted by R(max), is used to determine the uniform number of samples per beat for further processing. Note that in the following discussion, the terms PQ, QRS, and ST refer to blocks of data that approximate the clinically defined intervals.

In step 106, the ECG record is split into N individual beats at the junctions between the PQ and ST blocks for each beat (or record). The number of samples in each individual RR-interval is optionally retained for later reconstruction of the beats. In step 108, the beats are aligned at their R-peaks, such that the R peak falls at the same sample in each record; note that the records are not of uniform length. The PQ, QRS, and ST blocks are then designated, as per the description of FIG. 2.

In step 110, centered local averages are applied to the blocks of the individual records to reduce aliasing after downsampling. Since the downsampling rates will be different in the PQ, QRS and ST blocks, the size of the centered local average must be block-dependent. In the PQ and ST blocks, where power is negligible over 10 Hz, the downsampling rate will be higher, and so the width of the centered local average is chosen at 9 samples, to reduce power down to 10 Hz. The width of the centered local average applied to the QRS block is only 3 samples, so that power is reduced down to only 30 Hz.

In optional step 112, the PQ, QRS and ST blocks are downsampled. The sampling frequency of ECG recordings is typically chosen to resolve the QRS complex, and is typically set to around 360 Hz. The spectral density functions (SDFs) for each block indicate that power in the PQ and ST blocks is negligible over 10 Hz. The PQ and ST blocks are therefore conservatively downsampled at a rate of 72 Hz (i.e. every fifth point is retained), in order to resolve features at up to 36 Hz. The QRS block has power up to about 30 Hz, and contains most of the features of diagnostic interest; this block is therefore downsampled at a rate of 180 Hz (every other point is retained), in order to resolve features down to 90 Hz. The size of each sample beat is thereby greatly reduced, but the sample sizes are not uniform.

The downsampled traces are then padded in step 114; for example, the end data value is repeated at the beginning of the PQ block and the end of the ST block, so that the beat data sets are all of the same length (i.e., the length of the maximum RR-interval). The beats are now of uniform size.

In the PQ block, the number of samples is M(PQ)=(0.4R (max)−⅛)/D(PQ), where D(PQ) is the new sample time increment in the PQ block.

In the QRS block, the number of samples is M(QRS)=0.25/D(QRS), where D(QRS) is the new sample time increment in the QRS block.

In the ST block, the number of samples is M(ST)=(0.6R (max)−⅛)/D(ST), where D(ST) is the new sample time increment in the ST block.

Thus, the total number of samples in each beat is:

$$M=M(PQ)+M(QRS)+M(ST)$$

The N beat sets, each of length M, are loaded into a beat matrix having N rows (one per beat) and M columns. The i column consists of the i samples from each beat. Usually, N will be much greater than M.

In step 116, the M-dimensional Karhunen-Loeve Transform (KLT) of the N by M beat matrix is calculated. This is done by calculating the (positive definite symmetric) covariance matrix of the beat matrix, and then diagonalizing it (using Singular Value Decomposition) to determine its eigenvalues and eigenvectors. The beats are then transformed into the basis determined by the eigenvectors. This calculation produces several sets of data:

M positive eigenvalues for the covariance matrix. These are always positive numbers, because the covariance matrix is always positive definite. The i eigenvalue is the variance of the sample set in the i eigenvector of the covariance matrix. The largest eigenvalue corresponds to the eigenvector in which most of the sample variance occurs. The eigenvalues are then ordered from largest to smallest, in order to retain the maximum possible amount of variation detail when the data is compressed.

M orthonormal eigenvectors for the covariance matrix, which are placed in order corresponding to that of the eigenvalues.

An N by M transform matrix. The rows of the transform matrix contain the transform coefficients of the individual beat samples. That is, the value in the n row and m column of the transform matrix is the coefficient corresponding to the m eigenvector determined by the KLT, of the n beat.

In step 118, a variance criterion is used to determine which coefficients will be retained as data for use in reconstructing the original sample set. In the variance criterion, a value b between 0 and 1 is selected; b is usually selected to be close to one. The number of coefficients to be retained is m, where:

$$\sum_{i=1}^{m} \frac{\sigma_i^2}{V^2} > b$$

(here, V denotes the square root of the sum of the variances in the individual Karhunen-Loeve coefficients). The total data to be retained, when the variance criterion is used, is:

The m largest eigenvalues and their corresponding eigenvectors from the KLT,

The first m coefficients of each of the N beats in the transform matrix,

The size of the RR-interval corresponding to each beat.

This data is then stored.

In step 120, which is an alternative to step 118, a quality-controlled criterion is used to determine which coefficients from the transform matrix will be retained as data for use in reconstructing the original sample set. A value, e, between 0 and 1 is selected (it is chosen to be quite small). For the i beat, m(i) coefficients are to be retained; m(i) is chosen, individually for each beat, using a quality control measure.

We define X(i)^ to be an estimate of the i beat, constructed from the first k coefficients of the i beat with respect to the Karhunen-Loeve transform. The number m(i) of coefficients retained from the i beat is taken so that:

$$\frac{\|X_j(i)^\wedge - X_j(i)\|^2}{\|X_j(i)\|^2} < e$$

where the j indicates that the measure of error must be uniformly less than e in each of the three blocks j=PQ, QRS, and ST. In each case, eigenvectors and coefficients are added to the estimate in the same order, the one indicated by the sizes of the associated variances. The measure used is relative root mean square error, calculated individually in each of the three blocks. The total data to be retained, when the quality control criterion is used, is:

K eigenvalues and eigenvectors from the KLT, where K is the maximum value of m(i) over all N beats.

For the i beat, m(i) coefficients of the KLT.

The size of the RR-interval corresponding to each beat.

This data is then stored.

Figure 2:
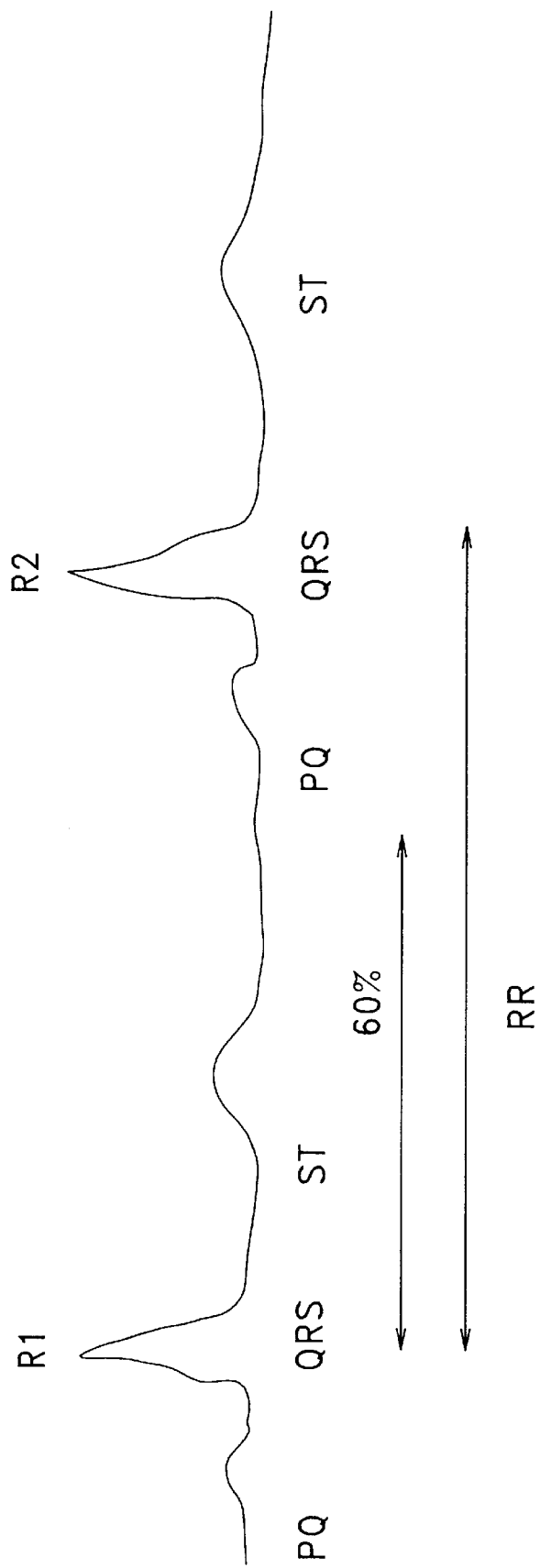
FIG. 2 is a timing diagram showing the blocking of a typical heartbeat, with PQ, QRS, and ST blocks diagrammed.

FIG. 2 is a diagram of the blocking 200 of a typical heartbeat. Again, note that in the following discussion, the terms PQ, QRS, and ST refer to blocks of data that approximate the clinically defined intervals. The locations of two R-peaks, R-peak 1 and R-peak 2, are indicated; these features are easily identified in an ECG. A QRS block is defined to be a 0.25-second wide window centered on an R-peak. The boundary between the PQ and the ST blocks is defined by determining the distance between successive R-peaks, and placing the boundary at 60% of the distance from one R-peak to the next. The ST block is therefore the first 60% of the interval between R-peaks, less ⅛ of a second of the preceding R-peak 1. The PQ block is the last 40% of the interval between R-peaks, less ⅛ of a second of the following R-peak 2.

Figure 3:
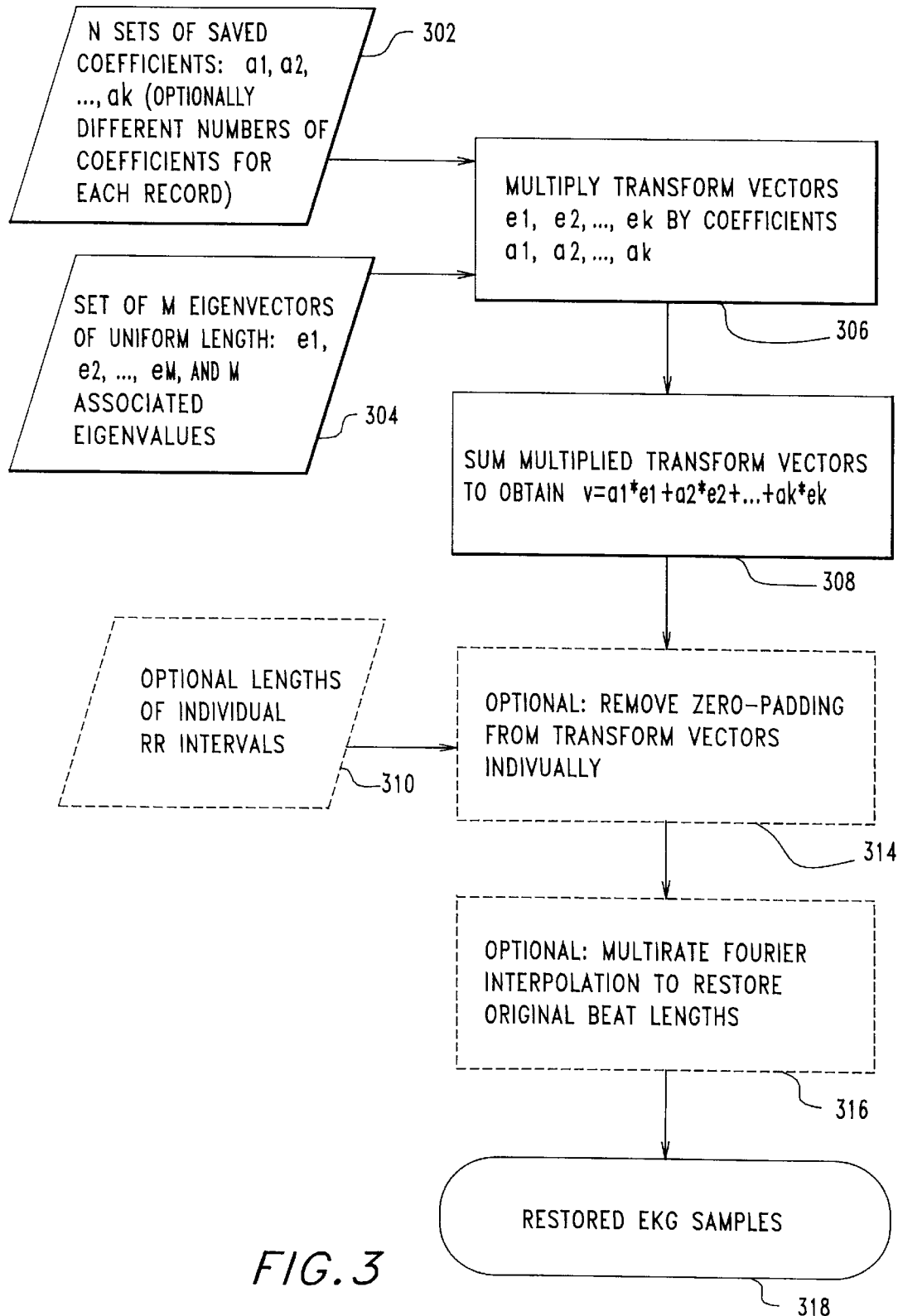
FIG. 3 is a flow diagram showing the flow of a reconstitution algorithm according to the present invention.

FIG. 3 is a flow diagram showing the steps of reconstituting the compressed heart beat data. The input to step 306, the first step of the reconstruction process, consists first of N sets of saved coefficients 302, where N is the total number of records in the data set. These are denoted a1,a2, . . . ,ak(n), where the value of k(n) is the number of KLT coefficients saved for the nth record. The coefficients {ai} are ordered within each compressed record, in accordance with the ordering of the eigenvectors and eigenvalues 304. If the variance criterion 118 is used in the compression process, the value of k(n) is fixed for all records: i.e., k(n)=k for all n{1, . . . ,N}. If the quality-controlled criterion 120 is used as an alternative to the variance criterion 118 in the compression process, then the value of k(n) varies with n, and serves as a rough indicator of the presence of exceptional features in the nth heartbeat (the higher the value of k(n), the more unusual features are likely to be found in the nth heartbeat). The second input to step 306 is the full set of M KLT eigenvectors 304 of uniform length M, and associtaed eigenvalues. The eigenvectors were ordered in accordance with the size of the eigenvalues of the cross-covariance matrix. These eigenvectors and eigenvalues are derived during the KLT transform step 116. M is the (fixed) length of the original downsampled and padded time-domain traces submitted to the KLT transform 116.

In step 306, the number of coefficients k(n) saved for each of the N records is determined, and the first k(n) eigenvectors {e1, . . . ,ek(n)} are multiplied by {a1, . . . ,ak(n)}, and then summed, to form:

$$v(n) = a1 \cdot \lambda 1 \cdot e1 + a2 \cdot \lambda 2 \cdot e2 + \ldots + ak(n) \cdot \lambda k(n) 1 \cdot ek(n)$$

Note that in this description, the terms "eigenvalue" and λ1–λk(n) refer to the square roots of the eigenvalues of the covariance matrix of the sample set. The coefficients a1–ak(n) are the result of factoring λ1–λk(n) out of the standard KLT transform coefficients.

Alternatively, the eigenvectors of the covariance matrix and the standard KLT transform coefficients could be retained in the conventional manner, but this is not quite as efficient in terms of storage space.

The vector v(n) is an approximation to the nth heartbeat vector within the compressed segment submitted to the KLT transform step 116, which is accurate to within the criteria established for compression in step 118 (variance-controlled criterion) or in step 120 (quality-controlled criterion).

In step 114, the traces were (optionally) padded to a uniform size: this padding can be removed, if desired, in step 314. The R peak falls at the same sample in each record. Since the total length 310 of the downsampled nth heartbeat is also known for each trace, the beginning of the PQ portion of the trace is truncated so that 40% of the total length of the nth trace is at the left of its R-peak after truncation. This is the correct length of the PQ portion of the trace. Similarly, the nth trace is truncated at the end of the ST portion of the trace, so that 60% of the total length of the nth trace is at the right of its R-peak after truncation. This is the correct length of the reconstituted, but still downsampled, ECG trace.

In step 316, a multirate Fourier interpolation may be applied, if multirate down-sampling was used, to restore the original lengths of the reconstituted ECG traces. This step is not strictly necessary, since by the Shannon sampling theorem, the downsampled traces contain the same spectral information as they would after interpolation to restore their original length. In step 112, the PQ, QRS, and ST blocks were downsampled at different rates in order to take advantage of the variable spectral densities in each block to maximize compression; therefore, the PQ, QRS, and ST blocks must be interpolated at different rates in order to reconstruct an approximation of the original block. Techniques for reconstructing a band-limited signal from its samples are well known to practitioners in the field. The final interpolation step yields ECG samples, restored to their original length.

Figure 4:
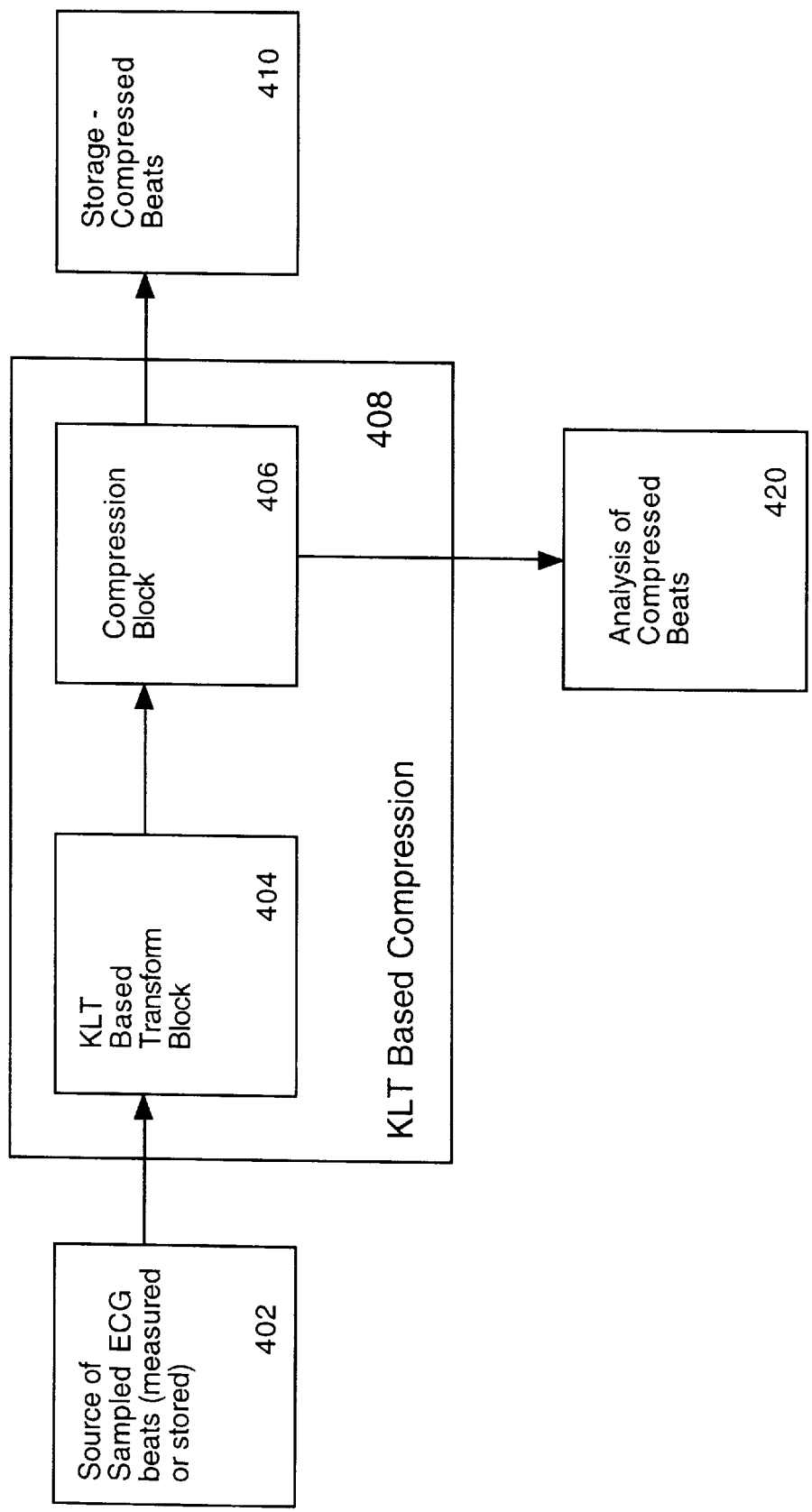
FIG. 4 is a block diagram of apparatus for implementing the compression algorithm of FIG. 1.

FIG. 4 is a block diagram showing apparatus for KLT based compression of sampled heart beats (ECGs). The source 402 of sampled heart beats, or records, may be storage of some sort, such as a file on a tape or a hard drive, or it may provide real time sampled heart beats from a patient. KLT based compression block 408 comprises a KLT Transform Block 404 and a compression block 406. KLT Transform Block 404 KLT transforms the plurality of records, resulting in a set of λ coefficients for each record, and a set of eigenvalues and eigenvectors for the set of records. The eigenvalues, their associated eigenvectors, and the coefficients are ordered according to decreasing size of the eigenvalues. The eigenvalues indicate which eigenvectors contain the most information. KLT transform block 404 may also perform the other functions specified in FIG. 1. For example, each record must be the same size prior to the KLT transform, and the R beats must be aligned.

Compression block 406 discards some of the λ coefficients for each record (the least significant, or last, coefficients). Compression block 406 also discards the least significant eigenvectors and eigenvalues. In the variance controlled criteria case, the m most significant λ coefficients for each record, and the m most significant eigenvectors and eigenvalues, are retained (with "m" being a calculated or predetermined value). The others are discarded, which accomplishes the compression function.

In the quality controlled criteria case, different numbers of λ coefficients are retained for each record. The most coefficients are retained for the most unusual heart beats, so the number of coefficients retained can be used to flag the interesting heart beats for analysis.

The compressed data may be stored in block 410 (as a file for example). Or, the compressed date may be reconstituted and analyzed, by a computer algorithm or by human observation.

Figure 5:
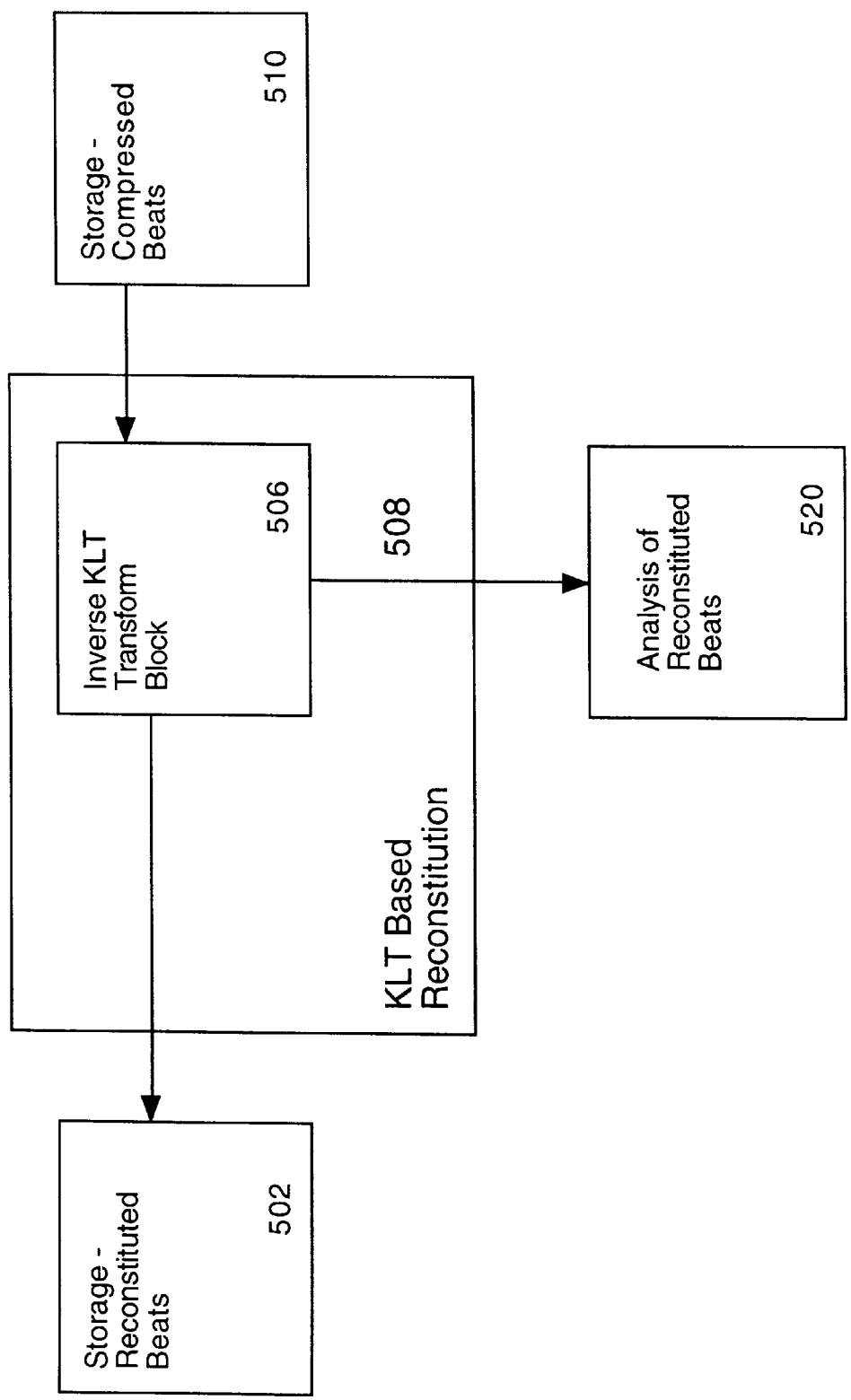
FIG. 5 is a block diagram of apparatus for implementing the reconstitution algorithm of FIG. 3.

FIG. 5 is a block diagram of apparatus for decompressing KLT compressed sampled heart beats. Block 510 indicates the storage device containing the compressed data. As an alternative, the compression could be done in real time with data from a patient. This might be useful in a device which detects unusual heart beats on the fly (by analysing the records having the most retained λ coefficients, e.g.). Block 506 inverse KLT transforms the records by multiplying the stored λ coefficients for each record by the eigenvectors for the data set. Also refer to FIG. 3 for other functions performed by inverse KLT block 504. The reconstituted beats may be stored in block 502 or analyzed in block 520.

What is claimed is:

1. A method of encoding a plurality of sampled ECG records, each record representing a heartbeat, said method comprising the steps of:
   (a) aligning the records about their R-peaks;
   (b) sizing the records to have the same number of samples and forming a sample set of the sized records; and (c) performing a Karhunen-Loeve Transform (KLT) on the sample set, thereby generating a set of eigenvalues and associated eigenvectors for the sample set, and a set of KLT coefficients for each record.

2. The method of claim 1, further including the steps of:
(d) ordering the eigenvalues and their associated eigenvectors in decreasing order of eigenvalue size; and
(e) retaining an ordered subset of the most significant KLT coefficients for each record and an ordered subset of the eigenvectors associated with largest eigenvalues for the sample set.

3. The method of claim 2, wherein the retaining step (e) further retains the m largest eigenvalues for the sample set.

4. The method of claim 3, wherein the retaining step (e) retains the same number m of KLT coefficients for each record and m eigenvectors and eigenvalues for the sample set.

5. The method of claim 3, wherein the retaining step (e) retains a variable number of KLT coefficients for each record, according to a criterion which minimizes reconstruction error.

6. The method of claim 2, wherein the retaining step (e) retains the same number m of KLT coefficients for each record and m eigenvectors for the sample set.

7. The method of claim 2, wherein the retaining step (e) retains a variable number of KLT coefficients for each record, according to a criterion which minimizes reconstruction error.

8. The method of claim 7 further including the step of flagging the records for which the most coefficients are retained, for analysis.

9. The method of claim 2, wherein the step of sizing (b) the records comprises the step of padding the ends of the shorter records.

10. The method of reconstituting a desired set of ECG records encoded according to the method of claim 2, comprising the steps of:
retrieving the retained ordered KLT coefficients for each record of the desired set and the retained ordered eigenvectors for the desired set; and
performing a reverse Karhunen-Loeve Transform (KLT) on the retrieved KLT coefficients and eigenvectors to generate a plurality of records.

11. The method of claim 2 further including the step of retaining the actual number of samples in each record prior to sizing each record.

12. The method of reconstituting a desired set of ECG records encoded according to the method of claim 11, comprising the steps of:
retrieving the retained ordered KLT coefficients for each record, actual number of samples for each record, and ordered eigenvectors for the desired set;
performing a reverse Karhunen-Loeve Transform (KLT) on the retrieved KLT coefficients and eigenvectors to generate a plurality of records; and
resizing each record according to the retrieved actual number of samples for that record.

13. The method of claim 2, further including the step of downsampling each record prior to forming the sample set.

14. The method of claim 13 wherein each record is downsampled at multiple rates, and wherein the downsampling is more severe at slowly varying portions of the record and less severe at quickly varying portions of the record.

15. The method of claim 14 wherein the step of downsampling at multiple rates downsamples the PQ and ST portions of the record at least about twice as heavily as the QRS portion of the record.

16. The method of reconstituting a desired set of ECG records encoded according to the method of claim 15, comprising the steps of:
retrieving the retained ordered KLT coefficients for each record, the actual number of samples for each record, and the ordered eigenvectors for the desired set;
performing a reverse Karhunen-Loeve Transform (KLT) on the retrieved KLT coefficients and eigenvectors to generate a plurality of records; and
upsampling each record at multiple rates selected to restore the original sample rate of each portion of the record.

17. Apparatus for encoding a plurality of sampled ECG records, each record representing a heartbeat, said apparatus comprising:
means for centering the records about their R-peaks;
means for sizing the records to have the same number of samples and forming a sample set of the sized records; and
means for performing a Karhunen-Loeve Transform (KLT) on the sample set, thereby generating a set of eigenvalues and eigenvectors for the sample set, and a set of KLT coefficients for each record.

18. The apparatus of claim 17, further comprising:
means for ordering the eigenvalues and their associated eigenvectors in decreasing order of eigenvalue size; and
means for retaining an ordered subset of the most significant KLT coefficients for each record and an ordered subset of the eigenvectors associated with largest eigenvalues for the sample set.

19. The apparatus of claim 18, wherein the means for retaining retains the same number m of KLT coefficients for each record and retains the m eigenvectors associated with the m largest eigenvalues for the sample set.

20. The apparatus of claim 18, wherein the means for retaining retains a variable number of KLT coefficients for each record, according to a criterion which minimizes reconstruction error, and retains enough eigenvectors associated with the largest eigenvalues to reconstitute the record for which the largest number of KLT coefficients are retained.

21. The apparatus of claim 20, further including means for flagging the records for which the most coefficients are retained, for analysis.

22. The apparatus of claim 18, further including means for downsampling each record at multiple rates prior to forming the sample set.

23. Apparatus for reconstituting a desired set of ECG records encoded by the apparatus of claim 18, comprising:
means for retrieving the retained ordered KLT coefficients for each record in the desired set and the retained ordered eigenvectors for the desired set; and
means for performing a reverse Karhunen-Loeve Transform (KLT) on the retrieved KLT coefficients and eigenvectors to generate a plurality of records.

24. A method of detecting irregular heartbeats from a string of sampled heartbeat records comprising the steps of:
(a) centering the records about their R-peaks;
(b) sizing the records to have the same number of samples and forming a sample set of the sized records;
(c) performing a Karhunen-Loeve Transform (KLT) on the sample set, thereby generating a set of eigenvalues and associated eigenvectors for the sample set, and a set of KLT coefficients for each record;
(d) ordering the eigenvalues and their associated eigenvectors in decreasing order of eigenvalue size;

(e) retaining an ordered subset of the most significant KLT coefficients for each record and an ordered subset of the eigenvectors associated with largest eigenvalues for the sample set wherein a variable number of KLT coefficients for each record is retained, according to a criterion which minimizes reconstruction error; and (f) flagging each record for which more than a predetermined number of coefficients are retained, as pertaining to potentially irregular heartbeats.

25. The method of claim 24, further including the step of: sounding an alarm if any records are flagged by step (f).

26. The method of claim 24, further including the step of: applying medication if any records are flagged by step (f).

27. The method of claim 24, further including the step of: reconstituting any flagged records by applying a reverse KLT to the coefficients for that record and the eigenvectors for the sample set; and displaying the reconstituted beats for analysis.

28. The method of claim 24, wherein the sampled heartbeat records are retreived from storage.

29. The method of claim 24, wherein the sampled heartbeat records are sampled in real time from a patient's monitored heartbeats.

* * * * *

UNITED STATES PATENT AND TRADEMARK OFFICE
CERTIFICATE OF CORRECTION

PATENT NO. : 6,152,883
DATED : November 28, 2000
INVENTOR(S) : Blanchett et al.

It is certified that error appears in the above-identified patent and that said Letters Patent is hereby corrected as shown below:

Title page, Item [54], and Column 1, line 1,
Title, delete "EGG" and insert -- ECG --.

Figure 3,
Box 318, delete "EKG" and insert -- ECG --.

Signed and Sealed this

Twelfth Day of March, 2002

*Attest:*

JAMES E. ROGAN
*Attesting Officer*  *Director of the United States Patent and Trademark Office*